United States Patent
Reitter et al.

(10) Patent No.: US 6,981,952 B2
(45) Date of Patent: Jan. 3, 2006

(54) APPARATUS FOR GENERATING ACOUSTIC WAVES

(75) Inventors: Josef Reitter, Moehrendorf (DE); Arnim Rohwedder, Fuerth (DE)

(73) Assignee: Siemens Aktiengesellschaft, Munich (DE)

( * ) Notice: Subject to any disclaimer, the term of this patent is extended or adjusted under 35 U.S.C. 154(b) by 569 days.

(21) Appl. No.: 09/809,958

(22) Filed: Mar. 16, 2001

(65) Prior Publication Data
US 2001/0046184 A1 Nov. 29, 2001

(30) Foreign Application Priority Data
Mar. 16, 2000 (DE) .............................. 100 12 878

(51) Int. Cl.
*A61N 7/00* (2006.01)

(52) U.S. Cl. .............................. 601/2; 601/4; 600/427; 367/142; 367/150

(58) Field of Classification Search ............... 601/2–4; 600/439, 427; 367/142, 150
See application file for complete search history.

(56) References Cited

U.S. PATENT DOCUMENTS

| | | | |
|---|---|---|---|
| 5,285,772 A | | 2/1994 | Rattner |
| 5,699,804 A | * | 12/1997 | Rattner ....................... 600/439 |
| 5,879,314 A | * | 3/1999 | Peterson et al. ................ 601/2 |
| 6,119,034 A | * | 9/2000 | Herrmann et al. ........... 600/427 |
| 6,383,152 B1 | * | 5/2002 | Hartmann et al. .............. 601/4 |

FOREIGN PATENT DOCUMENTS

DE 197 02 593 7/2000

* cited by examiner

*Primary Examiner*—Ruth S. Smith
(74) *Attorney, Agent, or Firm*—Schiff Hardin LLP

(57) ABSTRACT

An apparatus for generating acoustic waves has an acoustic transducer with a first electrode serving as a membrane and adjoining an acoustic propagation medium and a second electrode spaced from the first, between which an electrolyte is situated. The acoustic transducer is fashioned transparent to X-rays.

10 Claims, 2 Drawing Sheets

APPARATUS FOR GENERATING ACOUSTIC WAVES

BACKGROUND OF THE INVENTION

1. Field of the Invention

The invention is directed to an apparatus for generating acoustic waves of the type having an acoustic transducer with a first electrode serving as a membrane and adjoining an acoustic propagation medium, and a second electrode spaced from the first electrode, between which an electrolyte is situated.

2. Description of the Prior Art

An apparatus of the above type for generating acoustic waves operates according to the thermo-hydraulic principle. Due to the brief heating of the electrically conductive electrolyte situated between the electrodes by a filament voltage that flows as a result of an electrical pulse applied to the electrodes, electrical energy is directly converted into thermal energy of the electrolyte practically loss-free. The thermal expansion of the electrolyte produced by the filament current generates a pressure wave propagates in the acoustic propagation medium adjacent to the first electrode. Accordingly, the apparatus can be utilized, for example, for generating shock waves as employed in medicine in lithotripsy or in pain therapy.

An apparatus of the type initially described is disclosed in German OS 197 02 593. The apparatus has a first electrode which is a solid and a second, thin electrode serving as membrane between which the electrolyte is situated.

A disadvantage of the apparatus for generating acoustic waves disclosed in German OS 197 02 593 the use of x-rays to locate an object to be irradiated with sound with the apparatus—as is standard in lithotripsy for locating calculi—can ensue only when the apparatus is "behind" the x-rays. Consequently, the possibilities of X-ray locating at the apparatus are limited. This means that an attending physician can only see a part of the therapy region in the X-ray exposures for medical applications in lithotripsy.

SUMMARY OF THE INVENTION

An object of the present invention is to provide an apparatus of the type initially described with which the possibilities of X-ray locating at the apparatus are expanded.

According to the invention, this object is achieved in an apparatus for generating acoustic waves with an acoustic transducer having a first electrode serving as a membrane and adjoining an acoustic propagation medium and a second electrode spaced from the first, between which an electrolyte is situated, whereby the acoustic transducer is transparent to X-rays. As a result of the transparency of the acoustic transducer for X-rays, the overall apparatus can be fashioned transparent for X-rays according to one version of the invention, so that X-ray locating can ensue passing through the apparatus during the operation of the apparatus. The acoustic transducer, when used with an appropriately positioned X-ray source, which usually emits a cone-shaped X-ray beam relative to the apparatus, can have a radial extent so that practically no occlusion of the X-ray beam proceeding through the apparatus ensues due to the apparatus.

According to one embodiment of the invention, the X-ray-transparent electrodes each have a layer thickness in the micrometer range. The layer thickness of an electrode preferably amounts to 150 micrometers and less. In this way, even comparatively slight X-ray doses suffice in order to be able to transirradiate the electrodes and, thus, the acoustic transducer.

In a preferred embodiment of the invention, the electrodes have a uniform structure and smooth surfaces. In this way, X-ray images are obtained in the transirradiation of the acoustic transducer that are practically free of X-ray-positive superimpositions from the electrodes that would occur given a non-uniform structure of the electrodes. Since no superimpositions deriving from the acoustic transducer are present in X-ray images generated in this way, the probability of a misinterpretation of the X-ray images is nearly precluded.

Since the electrolyte employed in the acoustic transducer may be an aggressive substance that produces corrosion, in one embodiment of the invention the electrodes be fashioned of a corrosion-resistant material. According to one version of the invention, the electrodes are fashioned of stainless steel or aluminum.

When planar acoustic waves are generated with the acoustic transducer, in a further version of the invention the apparatus has an acoustic lens, preferably an acoustic positive lens, that focuses the acoustic waves onto a focus region. Such an acoustic lens for focusing the acoustic waves can, however, be foregone when, in another version of the invention, at least the first electrode, but preferably both electrodes, are fashioned concavely curved, so that a curved wave front is generated during the operation of the apparatus. Accordingly, the apparatus is self-focusing.

In another version of the invention the electrolyte flows through the space present between the first and second electrodes. In this way, operating conditions that are always defined can be maintained during operation of the apparatus. For example, with the flow-through it can be achieved that the electrolyte always exhibits the same initial temperature before the intentionally undertaken heating. To this end, the electrolyte can flow through a cooling device that keeps the temperature of the electrolyte constant.

DESCRIPTION OF THE PREFERRED EMBODIMENTS

Figure 1:
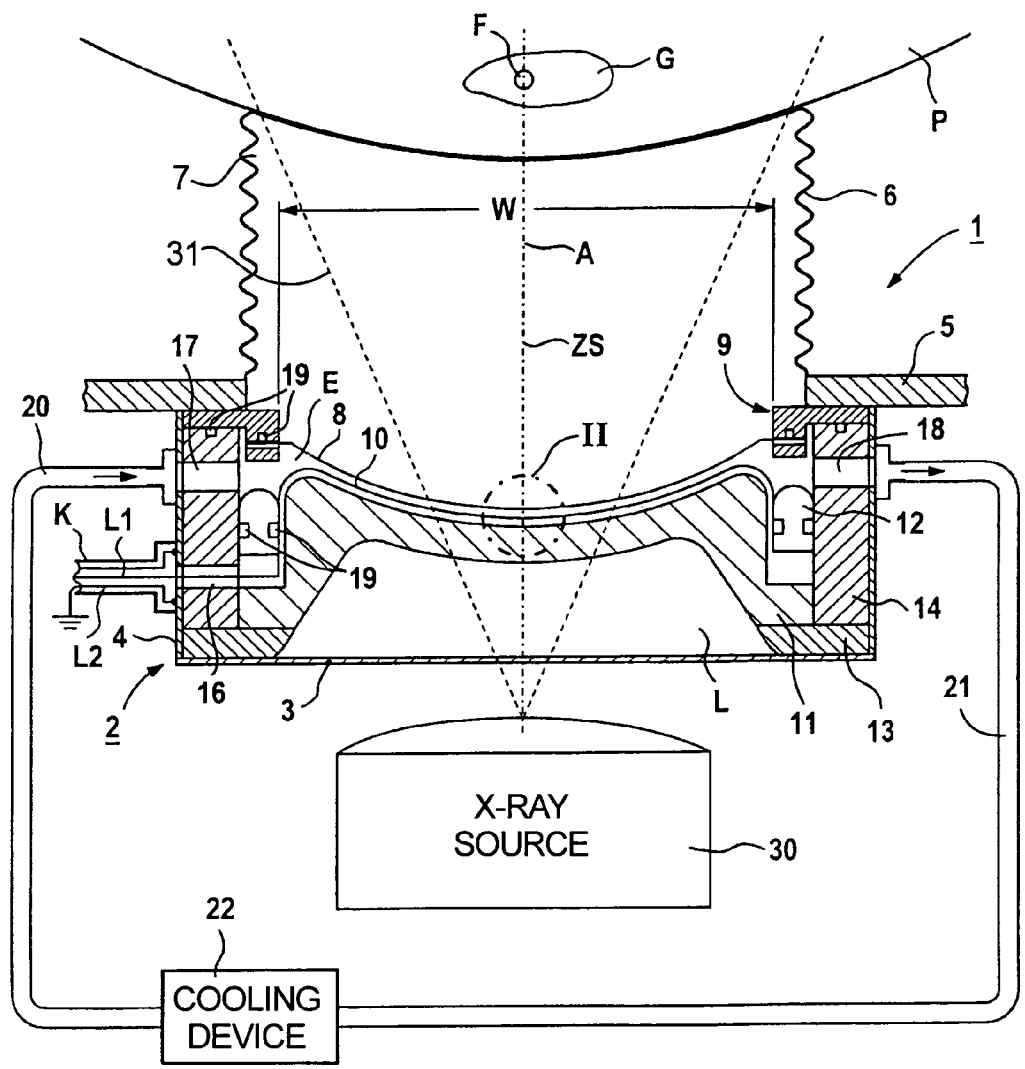
FIG. 1 is a sectional view of an inventive apparatus for generating acoustic waves.

The apparatus for generating shock waves shown in FIG. 1 in exemplary embodiment is a shock wave generator 1 that, for example, can be employed for lithotripsy or for pain therapy. The shock wave generator 1 is fashioned essentially dynamically balanced relative to its acoustic axis A and has a housing 2 of aluminum composed of a number of parts 3 through 5, the housing 2 serves for electrical shielding.

Figure 2:
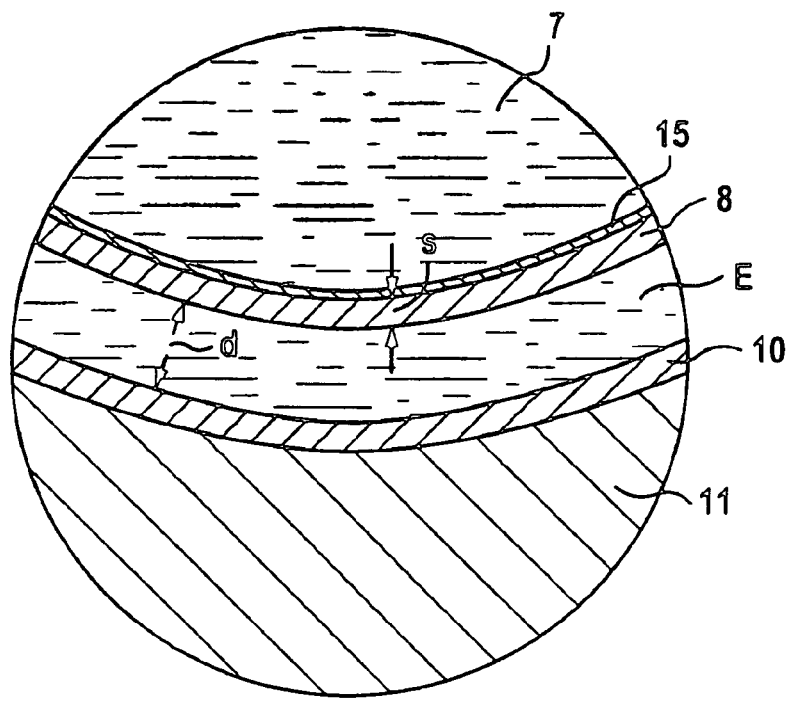
FIG. 2 is an enlarged portion of the apparatus of FIG. 1.

At the front side, the housing 2 is closed with a coupling bellows 6 schematically shown in FIG. 1 that can be applied against a patient P and that is filled with a propagation medium for acoustic waves, water 7 in the present case. A first circularly fashioned electrode 8 that serves as a membrane adjoins the water 7. The electrode 8 is fashioned concavely curved and has its outer edge fixed in a metallic clamp mechanism 9. A second electrode 10, which is likewise circularly fashioned and concavely curved, is arranged on an electrically insulating electrode carrier 11 made of plastic at a distance d from the first electrode 8. In an excerpt from FIG. 1, FIG. 2 shows the arrangement of the electrodes 8 and 10 relative to one another enlarged.

The outer edge of the electrode 10 is clamped between the electrode carrier 11 and an annular insulator 12. The electrode carrier 11 and the insulator 12 are seated against annular plastic parts 13, 14 that are seated against one another and against the housing parts 3 through 5. Air L is situated between the electrode carrier 11 and the housing part 3.

In the exemplary embodiment, both of the electrodes 8 and 10 are fashioned of corrosion-resistant aluminum and exhibit a uniform structure having a substantially constant layer thickness s of 100 micrometers and with smooth surfaces, i.e. a slight, substantially constant surface roughness. Moreover, that side of the electrode 8 facing toward the water 7 is provided with an electrically insulating coating 15 that is transparent for X-rays, but this is not compulsory.

The voltage feed at the shock wave generator 1 ensues coaxially. The housing part 4 as well as the plastic part 14 are provided with respective openings 16 through which a conductor L1 of a shielded cable K is conducted to the electrode 10, said cable K connecting the electrode 10 to a known power pulse generator (not shown). The electrode 8 fixed in the metallic clamp mechanism 9 is connected via the clamp mechanism to the housing 2, which is at ground potential via the conductor L2 of the cable K. Accordingly, the electrode 8 also is at ground potential.

A space filled with an electrolyte E is situated between the electrodes 8 and 10. The electrolyte E can be a conductive salt solution or a simple alcohol such as ethanol or methanol with ion-conductive additives. O-rings 19 are provided at the clamp locations of the electrodes 8 in the clamp mechanism 9, and at the clamp locations of the electrodes 10 between the electrode carrier 11 and the insulator 12, as well as between the annular plastic part 14 and the insulator 12, these O-rings prevent leakage of the electrolyte E from the space situated between the electrodes 8, 10 into the inside of the housing 2, from the housing 2 of the shock wave generator 1.

In the present exemplary embodiment, the electrolyte E flows through the space enclosed by the electrodes 8 and 10. The electrolyte E supplied to the space via an opening 17 in the housing part 4 and the plastic part 14 to which a conduit 20 is connected. The electrolyte E can flow out from the space between the electrodes 8 and 10 via a conduit 21 connected to a further opening 18 in the housing part 4 and the plastic part 14. During operation of the apparatus, the electrolyte E preferably circulates in a circulation through a cooling device 22 that keeps the electrolyte E at an approximately constant temperature. Moreover, means for degasification of the electrolyte E can be provided in the cooling device 22. Such gas can potentially form during operation of the apparatus and can negatively influence the function of the apparatus if it remains in the space between the electrodes 8 and 10 in the form of gas bubbles.

During operation of the apparatus, the power pulse generator driven by a control and computing unit (not shown in FIG. 1) applies voltage pulses to the electrodes 8 and 10 in a defined way, which produce a current flowing through the electrolyte E and as a result the electrolyte E is heated. The electrolyte E expands as a result of the heating, this being accompanied by a rise in pressure and, thus, the generation of a pressure wave. The pressure waves generated by the voltage pulses applied to the electrodes 8, 10 are introduced via the membrane 8 into the water 7 and from the latter into the body of the patient P via the coupling bellows 6. As a result of the concave curvature of the electrodes 8 and 10, the generated pressure waves intensify to form shock waves focussed onto a focus region F that are directed onto a tissue region G of the patient P to be treated. The directing of the shock waves usually ensues with X-ray locating.

As a result of the inventive embodiment of the shock save generator 1, the acoustic transducer of the shock wave generator 1, wherein the electrodes 8, 10, the electrode carrier 11, the electrolyte E and the propagation medium 7, are transparent to X-rays, so that X-ray locating can ensue passing through the shock wave generator 1.

FIG. 1 schematically shows an X-ray source 30 that emits a cone-shaped X-ray beam 31. The shock wave generator 1 and the X-ray source 30 are aligned relative to one another such that, first, the central ray ZS of the X-ray beam 31 emanating from the X-ray source 30 coincides with the acoustic axis A of the shock wave generator 1, and no occlusion of the cone-shaped X-ray beam 31 by the shock wave generator 1 ensues. This can be achieved by adapting the aperture width W of the shock wave generator 1 or of the acoustic transducer to the X-ray source 30 employed for the X-ray locating and selecting the spacing of the X-ray source 30 from the apparatus as small as possible. As a result of the construction of the shock wave generator 1 in conformity with the inventive principle, the shock wave generator, particularly the acoustic transducer of the shock wave generator, can accordingly be transirradiated with the X-rays. The components of the shock wave generator 1 other than the acoustic transducer lying in the space of the shock wave generator 1 to be transirradiated by the X-ray beam, such as the housing part 3, the water 7 (whose X-ray transparency is similar to that of human tissue), and the coupling bellows, thereby form no barrier for the X-radiation.

It is a significant advantage that the electrodes 8, 10 have only a slight layer thickness s, a uniform structure and smooth surfaces, so that no structures of the electrodes 8, 10 transirradiated with the X-radiation are imaged in the X-ray images.

As a result of the inventive structure of the shock wave generator 1, the structural height of the shock wave generator 1 can be kept comparatively small. In practice, the structural height can amount to only approximately half of the distance of the focus F from the electrode of the acoustic transducer serving as membrane. In this way, the distance that the X-ray beam 31 must cover when passing through the shock wave generator 1 can be kept relatively small. As a result, problems due to occlusions of the X-ray beam 31 can be largely avoided.

The electrolyte E, moreover, need not necessarily flow through the space enclosed by the electrodes 8 and 10. The electrolyte E alternatively can be kept stationarily enclosed in the space.

Figure 3:
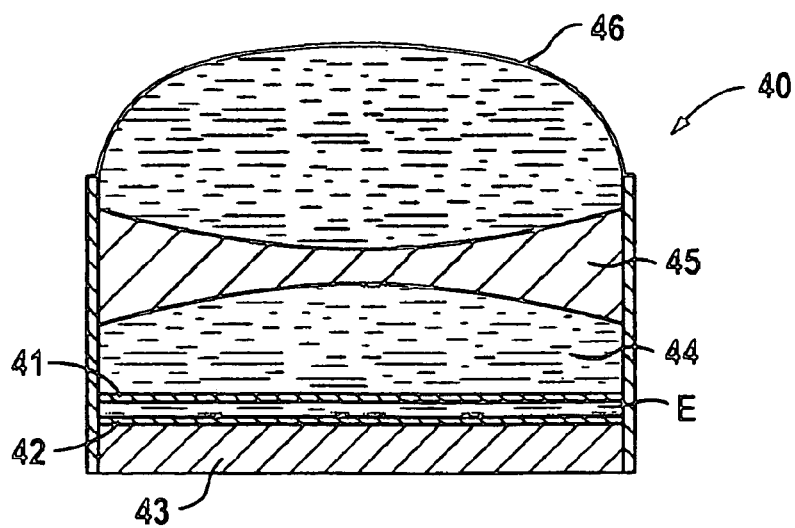
FIG. 3 shows an inventive apparatus for generating acoustic waves having an optical lens.

In the exemplary embodiment, the electrodes 8 and 10 are implemented concavely curved. The electrodes, however, can also be of a planar circular shape. In a highly schematic fashion, FIG. 3 shows a shock wave generator 40 having two planar, circular electrodes 41, 42 between which an electrolyte E is situated. The electrode 42 is arranged on an electrode carrier 43 of plastic. The electrode 41, which serves as membrane, has its side facing toward the acoustic propagation medium 44 provided with an electrically insulating coating (not visible in FIG. 3), like the electrode 8. Since only planar acoustic pressure waves can be generated with the acoustic transducer, an acoustic positive lens 45 for focussing the pressure waves generated with the acoustic transducer is provided in the case of the shock wave generator 40 shown in FIG. 3. The lens 45 is arranged within the shock wave generator in the acoustic propagation medium 44 and between the electrode 41 and the coupling bellows 46 that closes the shock wave source. In order to be able to transirradiate the shock wave generator with X-rays, the acoustic positive lens 45 is also fashioned of an X-ray-transparent material, for example polystyrol.

The inventive apparatus is described above with reference to the example of two shock wave generators 1, 40 that are provided for medical use. The employment of the apparatus, however, is not limited to the field of shock wave generation nor to the medical field.

Differing from the present exemplary embodiments, the electrodes can have different layer thicknesses and can be fashioned from other materials, for example stainless steel. The layer thickness as well as the selection of material is dependent on the respective application.

Although modifications and changes may be suggested by those skilled in the art, it is the intention of the inventors to embody within the patent warranted hereon all changes and modifications as reasonably and properly come within the scope of their contribution to the art.

We claim as our invention:

1. An apparatus for generating acoustic waves comprising:
    a volume containing an acoustic propagation medium;
    an acoustic transducer comprising a first electrode, operating as a membrane and disposed adjacent to said acoustic propagation medium, a second electrode spaced from said first electrode, a carrier comprised of x-ray transparent material on which said second electrode is disposed, and an electrolyte contained between said first electrode and said second electrode, each of first and second electrodes having a thickness making each of said first and second electrodes substantially transparent to X-rays; and
    circuitry connected to said first and second electrodes for briefly heating said electrolyte to displace said membrane to produce an acoustic wave in said acoustic propagation medium.

2. An apparatus as claimed in claim 1 comprising a housing containing said acoustic transducer and said volume, and wherein said housing is substantially transparent to X-rays.

3. An apparatus as claimed in claim 1 wherein each of said first electrode and said second electrode has a thickness in a micrometer range.

4. An apparatus as claimed in claim 1 wherein each of said first and second electrodes has a uniform structure and smooth surfaces.

5. An apparatus as claimed in claim 1 wherein each of said first and second electrodes is comprised of corrosion-resistant material.

6. An apparatus as claimed in claim 1 wherein each of said first and second electrodes is comprised of stainless steel.

7. An apparatus as claimed in claim 1 wherein each of said first and second electrodes is comprised of aluminum.

8. An apparatus as claimed in claim 1 further comprising an acoustic lens disposed in a propagation path of said acoustic wave.

9. An apparatus as claimed in claim 1 wherein at least said first electrode is concave, for focusing said acoustic wave.

10. An apparatus as claimed in claim 1 further comprising a circulatory system in fluid communication with a space containing said electrolyte between said first electrode and said second electrode, for circulating said electrolyte through said space.

* * * * *